(12) United States Patent
Kim

(10) Patent No.: US 7,048,701 B2
(45) Date of Patent: May 23, 2006

(54) LIE-DOWN MASSAGER

(76) Inventor: Hakjin Kim, 610 Ridgeview Ct., Diamond Bar, CA (US) 91765

( * ) Notice: Subject to any disclaimer, the term of this patent is extended or adjusted under 35 U.S.C. 154(b) by 494 days.

(21) Appl. No.: 10/249,567

(22) Filed: Apr. 18, 2003

(65) Prior Publication Data

US 2004/0210174 A1    Oct. 21, 2004

(51) Int. Cl.
*A61H 15/00* (2006.01)
(52) U.S. Cl. .......................... 601/99; 601/19; 601/100; 601/102; 601/103
(58) Field of Classification Search ................ 601/15, 601/18, 19, 86–103, 115–118, 126; 606/240–242; 5/617, 618
See application file for complete search history.

(56) References Cited

U.S. PATENT DOCUMENTS

| | | | |
|---|---|---|---|
| 4,422,449 A | 12/1983 | Hamabe | |
| 5,179,940 A | 1/1993 | Barreiro | |
| 6,629,939 B1 | 10/2003 | Jikiba et al. | |
| 6,643,551 B1 | 11/2003 | Park | |
| 6,656,138 B1 * | 12/2003 | Kim | 601/19 |
| 6,911,012 B1 * | 6/2005 | Kahn | 601/99 |
| 2003/0018284 A1 * | 1/2003 | Lim | 601/98 |

* cited by examiner

*Primary Examiner*—Quang D. Thanh
(74) *Attorney, Agent, or Firm*—Park Law Firm; John K. Park

(57) ABSTRACT

A lie-down massager comprises a frame having an elongated top panel with an elongated opening, a rider below the top panel, a guide member movably engaged between the base frame and the rider to enable the rider to make a horizontal reciprocation relative to the frame, and a lifter moving vertically relative to the rider. A shaft is rotatably engaged to the rider and eccentrically connected to a cam so the shaft rotation generates an eccentric rotation of the cam defined by an inner disk, an outer ring, and ball bearings circularly provided between the inner and outer disks where an outer rim of the outer ring abuts to a bottom of the lifter so the shaft rotating further generates vertical reciprocation of the lifter relative to the rider by the eccentric rotation of the cam.

35 Claims, 4 Drawing Sheets

LIE-DOWN MASSAGER

BACKGROUND OF INVENTION

The invention relates generally to a massaging device. More particularly, the present invention relates to an improved lie-down massager capable of efficiently treating bodily malfunctions such as back pain and gastrointestinal weakness by applying a therapeutic massaging treatment along the back and neck of a patient lying down on the massager whose massaging bumps move horizontally and vertically along the patients spinal cord and neck while the vertical movement of the massaging bumps are actuated by a cam mechanism.

Conventional bed or mat type massaging devices employ a spring mechanism for vertically moving massaging bumps. As disclosed U.S. Pat. No. 6,454,732, a spring mechanism allows the massaging bumps to gently move up and down. However, when it comes to therapeutic effects, the spring mechanism proves too soft to push up the massaging bumps when stronger pressure is required, because tension of springs applies equally to patients lying on the massaging device regardless of patients requirements.

A demand is to adopt a reliable mechanism demonstrating a steady and robust therapeutic effects while stabilizing the vertical movement of the massaging bumps.

SUMMARY OF INVENTION

The present invention is contrived to overcome the conventional disadvantages. Accordingly, an object of the invention is to provide a lie-down massager that improves therapeutic effects by adopting a cam mechanism for a vertical movement of massaging bumps.

Another object is to stabilize the vertical movement of the massaging bumps, thereby enabling patients to receive a steady and robust massaging of the massaging bumps applied to and along their backs and necks. A further object is to improve product reliability and customer satisfaction by mechanically stabilizing the vertical movement of the massaging bumps in accordance with a cam-shaft construction.

To achieve these and other objects, the lie-down massager according to the present invention comprises a base frame having an elongated top panel with an elongated opening formed centrally and lengthwisely through the elongated top panel. A rider is provided below the elongated top panel of the base frame, and a guide member is movably engaged between the base frame and the rider so as to enable the rider to make a horizontally reciprocal movement relative to the base frame. A lifter having a top portion and a bottom portion is provided such that elongated guides extend marginally from the bottom portion of the lifter. The elongated guides are releasably received by guide bushes formed on top of the rider to stabilize a vertically reciprocal movement of the lifter relative to the rider.

For a better performance, a shaft is rotatably engaged to the rider and eccentrically connected to a cam disk so that the shaft rotation generates an eccentric rotation of the cam disk. The cam disk is defined by an inner disk section, an outer ring section, and ball bearings circularly provided between the inner disk section and the outer ring section where an outer rim of the outer ring section abuts to the bottom portion of the lifter, whereby the shaft rotating further generates the vertically reciprocal movement of the lifter relative to the rider in accordance with the eccentric rotation of the cam disk while the outer rim of the outer ring section of the cam disk oscillatingly abuts to the bottom portion of the lifter. Massage bumps are attached to the top portion of the lifter and moving vertically and/or horizontally along the elongated opening of the elongated top panel of the base frame. There is also provided a pad covering the massage bumps and the elongated opening of the base frame.

In an embodiment, a pair of rack gears are provided below the elongated top panel of the base frame and the rack gears are parallel to each other, and a rider having a roller gear perpendicular to the rack gears where the roller gear is rotatably mounted on the rack gears to allow the rider to make a horizontally reciprocal movement along the rack gears. Here, the rider is maintained below the elongated top panel.

A pair of roller coasters parallel to each other and to the rack gears may be attached to the base frame and above the roller gear to allow the horizontally moving rider to pass therebetween where the roller coasters each have a substantially waved top surface. Here, a coasting member having a bottom surface and side surfaces is liftedly engaged to the rider. A guide roller is formed outwardly extending from the side surfaces of the coasting member so the guide roller on each of the side surfaces enables the coasting member to make a roller coasting movement on and along the waved top surfaces of the roller coasters while being engagedly lifted from the rider which makes the horizontally reciprocal movement. The roller coasters each substantially form a curvature of a human spinal cord.

The massage bumps are preferably partitioned to first and second pairs so the first pair bumps are aligned parallel to the second pair bumps. Each massage bump may include a heater or a heating lamp. First and second bump holders propping and maintaining the first and second pair bumps above the top portion of the lifter are tapered toward each lower end thereof. There may be further provided a first engagement member to rockingly engage the lower ends of the bump holders to the top portion of the lifter and a second engagement member to rollingly engage the massage bumps thereto.

Advantages of the present inventions are numerous. Most of all, the cam-shaft mechanism adopted for the vertical movement of the massaging bumps stabilizes power transmission from the cam motor to the lifter while facilitating control of massaging strength, thereby improving therapeutic effects of the massager. In addition, the oscillating motion of the cam disk along the bottom portion of the lifter further accelerates massaging effects of the massage bumps that make a free rocking depending on the curvature of the bodily portion being massaged, thereby improving product reliability. Further, the coasting member working with the roller coasters to realize an additional lifting by utilizing the horizontally reciprocal movement of the rider enables the massaging bumps to continue a smooth, steady and robust massaging on the patient, thereby substantially improving massaging effect and subsequently maximizing customer satisfaction.

Although the present invention is briefly summarized, the full understanding of the invention can be obtained by the following drawings, detailed description and appended claims.

BRIEF DESCRIPTION OF DRAWINGS

These and other features, aspects and advantages of the present invention will become better understood with reference to the accompanying drawings, wherein.

DETAILED DESCRIPTION

Figure 1:
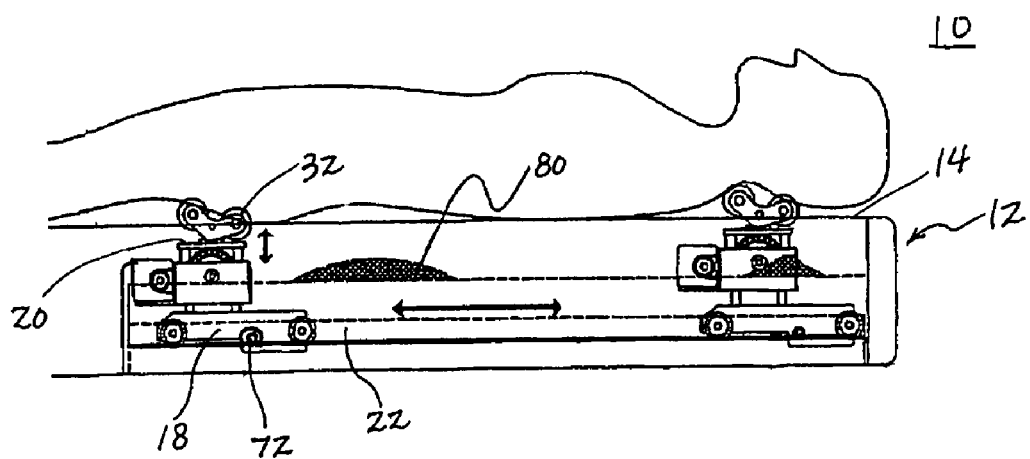
FIG. 1 is a view showing a lie-down massager with a patient lying thereon according to the present invention.
Figure 2:
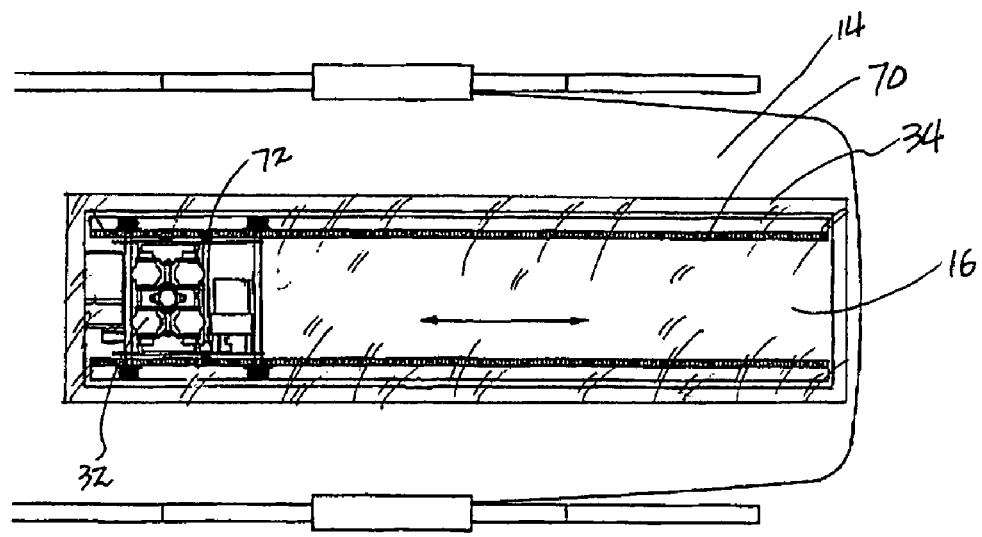
FIG. 2 is a plan view showing the lie-down massager without the patient in FIG. 1.

FIG. 1 shows a brief massaging mechanism of a lie-down massager 10 according to the present invention with a patient lying thereon for a bodily massage, and FIG. 2 shows a plan view of the massager 10 excluding the patient. As shown therein, the lie-down massager 10 includes a base frame 12 in a bed type or a mat type. The base frame 12 includes an elongated top panel 14, and an elongated opening 16 is formed centrally and lengthwisely through the elongated top panel 14. The massager 10 includes a rider 18 and a lifter 20. The rider 18 is provided below the elongated top panel 14 of the base frame 12. A guide member 22 is movably engaged between the base frame 12 and the rider 18 so as to enable the rider 18 to make a horizontally reciprocal movement relative to the base frame 12. Here, the guide member 22 may be formed of either a rope-pulley mechanism or a rack gear mechanism.

Figure 3:
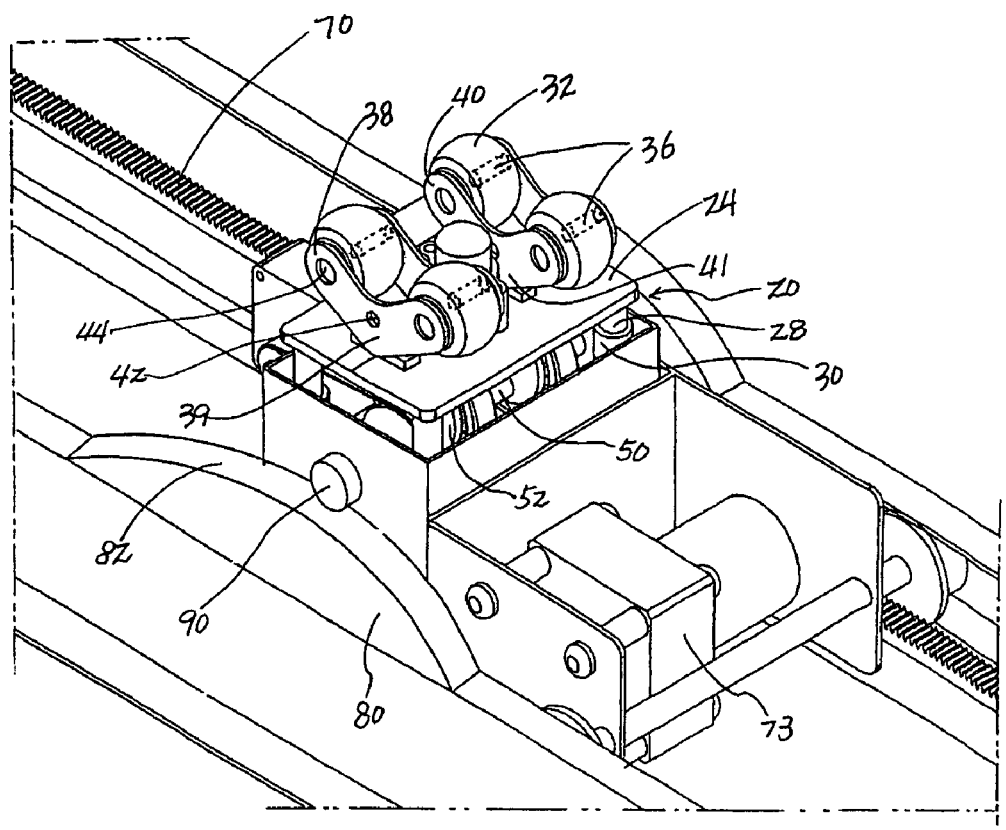
FIG. 3 is a partial perspective view showing an overall mechanism of the lie-down massager according to the present invention.
Figure 4:
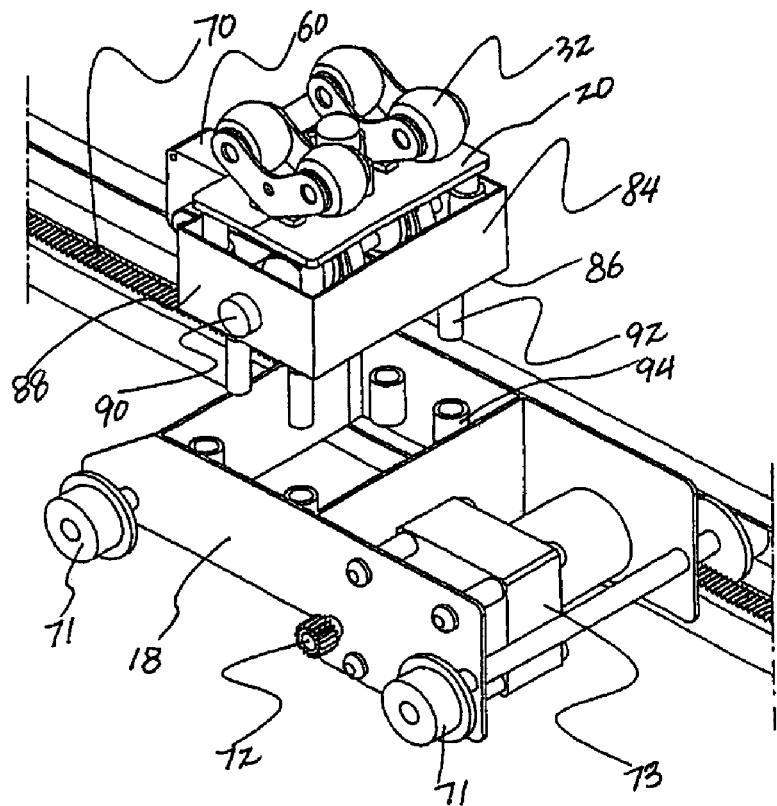
FIG. 4 is an exploded view of FIG. 3.

In FIGS. 2, 3 and 4, the massaging mechanism in FIG. 1 is further illustrated in perspective views. As shown therein, the lifter 20 has a top portion 24 and a bottom portion 26. In this construction, elongated guides 28 extend marginally from the bottom portion 26 of the lifter 20. The elongated guides 28 are releasably received by guide bushes 30 formed on top of the rider 18 so as to stabilize a vertically reciprocal movement of the lifter 20 relative to the rider 18. In a better version, the elongated guides 28 are formed in pins and the guide bushes 30 are formed in pin-receiving bushes.

In order to implement a therapeutic massage operation, a plurality of massage bumps 32 are attached to the top portion 24 of the lifter 20. The massage bumps 32 are provided to move vertically and/or horizontally along the elongated opening 16 of the elongated top panel 14 of the base frame 12. So the massage bumps 32 are directed to massage the back and neck of the patient lying on the top panel 14 of the base frame 12. Here, a pad 34 may be provided to cover the massage bumps 32 and the elongated opening 16 of the base frame 12.

The massage bumps 32 are preferably partitioned to first and second pairs so that the first pair bumps are aligned parallel to the second pair bumps. It is also recommended that the massage bumps 32 are formed of roller balls which are preferably formed of precious stone such as jade or gem. For a better massaging result, the massage bumps 32 may each include a heater 36 preferably in form of a heating lamp. Selectively, the heating lamp for the heater 36 may be formed to generate heat and infrared rays to maximize therapeutic effects. In a preferred mode, first and second bump holders 38, 40 are provided to prop and maintain the first and second pair bumps above the top portion 24 of the lifter 20. The first and second bump holders 38, 40 are tapered toward each lower end 39, 41 thereof. To improve flexibility of engagement between the bump holders 38, 40 and the bumps 32, and between the bump holders 38, 40 and the lifter 20, there are provided first and second engagement members 42, 44. The first engagement member 42 is provided to rockingly engage the lower ends 39, 41 of the bump holders 38, 40 to the top portion 24 of the lifter 20. The second engagement member 44 is provided to rollingly engage the massage bumps 32 to itself.

The engagement members 42, 44 each may be a bolt, a roller, or other engagement tool. In this bump-holder mechanism, the bump holders 38, 40 flexibly engaging the massage bumps 32 to the top portion 24 of the lifter 20 so that the massage bumps 32 rollingly massage the back and neck of the patient lying on the base frame 12 while evenly spreading the massaging power along the bodily portions being pushed up by the massage bumps 32. That is, the rocking mechanism of the bump holders 38, 40 enables the massage bumps 32 to smoothly follow the curvature of a spinal cord of the patient lying on the base frame 12 while each of the massage bumps 32 evenly delivers the massaging power to the patients bodily portions being massaged.

Figure 5:
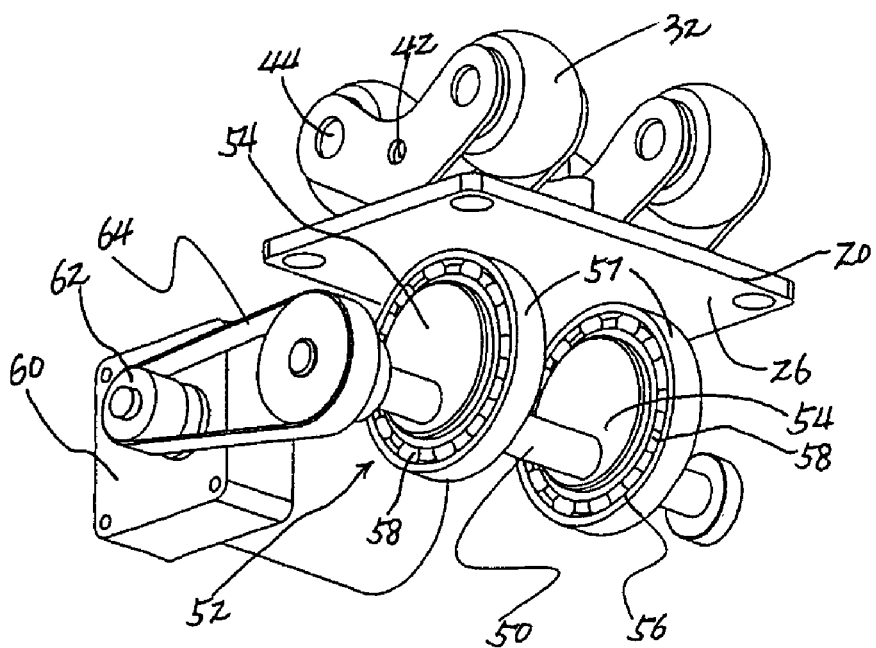
FIG. 5 is a partial view showing a cam mechanism of the lie-down massager according to the present invention.
Figure 6A:
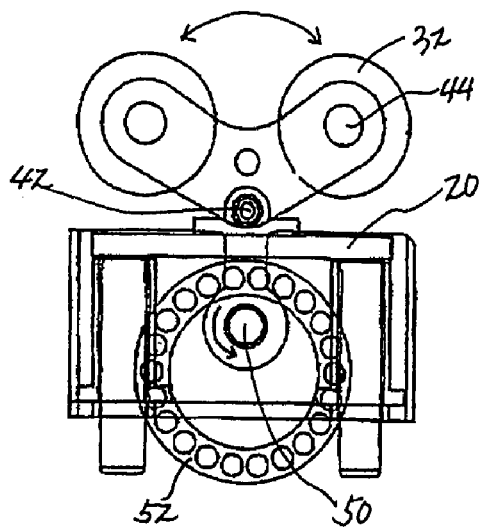
FIGS. 6A–6D are views showing a cam-applied lifting mechanism of the lie-down massager according to the present invention.
Figure 6B:
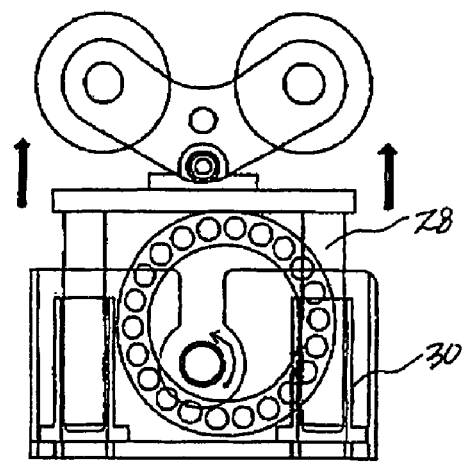
Figure 6C:
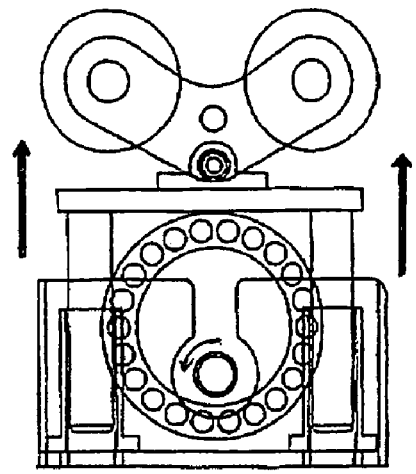
Figure 6D:
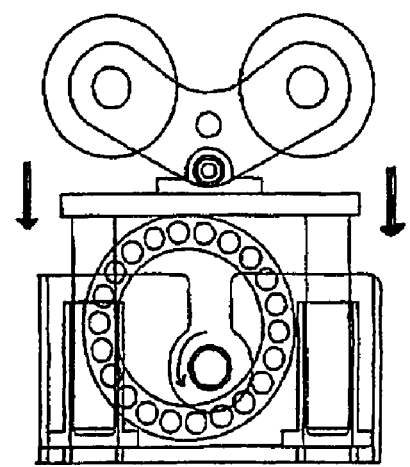

As further shown in FIGS. 3 and 5, there is provided a shaft 50 rotatably engaged to the rider 18. The shaft 50 is eccentrically connected to a cam disk 52 so that the shaft rotation generates an eccentric rotation of the cam disk 52. The cam disk 52 is defined by an inner disk section 54, an outer ring section 56, and ball bearings 58. The ball bearings 58 are circularly provided between the inner disk section 54 and the outer ring section 56. Here, an outer rim 57 of the outer ring section 56 abuts to the bottom portion 26 of the lifter 20.

FIGS. 6A–6D sequentially illustrate the cam-applied lifting mechanism of the lifter 20 in accordance with the rotation of the shaft 50. As shown therein, the rotation of the shaft 50 further generates the vertically reciprocal movement of the lifter 20 relative to the rider 18 in accordance with the eccentric rotation of the cam disk 52 while the outer rim 57 of the outer ring section 56 of the cam disk 52 oscillatingly abuts to the bottom portion 26 of the lifter 20. Preferably, the cam disk 52 may be formed in pair to further stabilize the vertical reciprocal movement of the lifter 20. In order to rotate the shaft 50, a cam motor 60 having a motor shaft 62 may be provided so that the motor shaft 62 is parallel to the cam shaft 50. Here, a timing belt 64 is carried on the motor shaft 62 and the cam shaft 50 to improve efficiency of the lifter-lifting mechanism.

In a preferred embodiment, a pair of rack gears 70 parallel to each other are provided below the elongated top panel 14 of the base frame 12. A roller gear 72 formed in the rider 18 is provided perpendicular to the rack gears 70 so the roller gear 72 is rotatably mounted on the rack gears 70 to allow the rider 18 to make a horizontally reciprocal movement along the rack gears 70 where the rider 18 is also maintained below the elongated top panel 14 of the base frame 12. Here, a plurality of guider rollers 71 may be formed from each side of the rider 18 to further stabilize the horizontally reciprocal movement of the rider 18 along the rack gears 70. The roller gear 72 is powered by a roller gear motor 73.

As further shown in FIGS. 3 and 4, another preferred embodiment adopts a roller coasting mechanism. As shown therein, a pair of roller coasters 80 parallel to each other and to the rack gears 70 are attached to the base frame 12 and above the roller gear 72 to allow the horizontally moving rider to pass therebetween. The roller coasters 80 are each formed to have a substantially waved top surface. In this construction, a coasting member 84 having a bottom surface 86 and side surfaces 88 is liftedly engaged to the rider 18. A guide roller 90 is formed outwardly extending from the side surfaces 88 of the coasting member 84. Here, the guide roller 90 on each of the side surfaces 88 enables the coasting member 84 to make a roller coasting movement on and along the waved top surfaces 82 of the roller coasters 80 while being engagedly lifted from the rider 18 which makes the horizontally reciprocal movement. Preferably, the coasting member 84 is formed in a container type.

So the first elongated guides 28 come to be releasably received by the first guide bushes 30 marginally formed on top of the coasting member 84 in order to stabilize the vertically reciprocal movement of the lifter 20 relative to the coasting member 84. In the better version, the waved top surfaces 82 of the roller coasters 80 each substantially form a curvature of a human spinal cord. Meanwhile, second elongated guides 92 are provided extending from the bottom surface 86 of the coasting member 84, and second guide bushes 94 are upwardly formed on the rider 18 to releasably receive the second elongated guides 92 so as to stabilize the roller coasting movement of the coasting member 84 along the roller coasters 80 and the lifting of the coasting member 84 from the rider 18.

As discussed above, an advantage of the lie-down massager 10 is that the cam-shaft mechanism adopted for the vertical movement of the massaging bumps 32 stabilizes power transmission from the cam motor 60 to the lifter 20 while facilitating control of massaging strength, thereby improving therapeutic effects of the massager 10. Another advantage is that the oscillating motion of the cam disk 52 along the bottom portion 26 of the lifter 20 further accelerates massaging effects of the massage bumps 32 that make a free rocking depending on the curvature of the bodily portion being massaged, thereby improving product reliability.

Further, the coasting member 84 working with the roller coasters 80 to realize an additional lifting by utilizing the horizontally reciprocal movement of the rider 18 enables the massaging bumps 32 to continue a smooth, steady and robust massaging on the patient, thereby substantially improving massaging effect and subsequently maximizing customer satisfaction.

Although the invention has been described in considerable detail, other versions are possible by converting the aforementioned construction. Therefore, the scope of the invention shall not be limited by the specification specified above and the appended claims.

What is claimed is:

1. A lie-down massager, comprising:
a) a base frame having an elongated top panel, wherein an elongated opening is formed centrally and lengthwisely through the elongated top panel;
b) a rider provided below the elongated top panel of the base frame;
c) a guide member movably engaged between the base frame and the rider so as to enable the rider to make a horizontally reciprocal movement relative to the base frame;
d) a lifter having a top portion and a bottom portion, wherein elongated guides extend marginally from the bottom portion of the lifter, wherein the elongated guides are releasably received by guide bushes formed on top of the rider to stabilize a vertically reciprocal movement of the lifter relative to the rider;
e) a shaft rotatably engaged to the rider, wherein the shaft is eccentrically connected to a cam disk so that the shaft rotation generates an eccentric rotation of the cam disk, wherein the cam disk is defined by an inner disk section, an outer ring section, and ball bearings circularly provided between the inner disk section and the outer ring section, wherein an outer rim of the outer ring section abuts to the bottom portion of the lifter, whereby the shaft rotating further generates the vertically reciprocal movement of the lifter relative to the rider in accordance with the eccentric rotation of the cam disk while the outer rim of the outer ring section of the cam disk oscillatingly abuts to the bottom portion of the lifter;
f) massage bumps attached to the top portion of the lifter and moving vertically and/or horizontally along the elongated opening of the elongated top panel of the base frame; and
g) a pad covering the massage bumps and the elongated opening of the base frame.

2. The lie-down massager of claim 1 wherein the massage bumps are partitioned to first and second pairs, wherein the first pair bumps are aligned parallel to the second pair bumps.

3. The lie-down massager of claim 1 wherein the massage bumps each include a heater.

4. The lie-down massager of claim 3 wherein the heater is a heating lamp generating heat and infrared rays.

5. The lie-down massager of claim 2 further comprising:
a) first and second bump holders propping and maintaining the first and second pair bumps above the top portion of the lifter, wherein the first and second bump holders are tapered toward each lower end thereof; and
b) a first engagement member to rockingly engage the lower ends of the bump holders to the top portion of the lifter.

6. The lie-down massager of claim 5 further comprising a second engagement member to rollingly engage the massage bumps thereto.

7. The lie-down massager of claim 1 wherein the massage bumps are roller balls.

8. The lie-down massager of claim 7 wherein the roller balls are formed of jade.

9. The lie-down massager of claim 1 wherein the cam disk is formed in pair.

10. The lie-down massager of claim 1 wherein the elongated guides are shaped in pins.

11. The lie-down massager of claim 1 further comprising:
a) a motor having a motor shaft parallel to the cam shaft; and
b) a timing belt carried on the motor shaft and the cam shaft.

12. A lie-down massager, comprising:
a) a base frame having an elongated top panel, wherein an elongated opening is formed centrally and lengthwisely through the elongated top panel;
b) a pair of rack gears provided below the elongated top panel of the base frame, wherein the rack gears are parallel to each other;
c) a rider having a roller gear perpendicular to the rack gears, wherein the roller gear is rotatably mounted on the rack gears to allow the rider to make a horizontally reciprocal movement along the rack gears, wherein the rider is maintained below the elongated top panel;
d) a lifter having a top portion and a bottom portion, wherein elongated guides extend marginally from the bottom portion of the lifter, wherein the elongated guides are releasably received by guide bushes marginally formed on top of the rider to stabilize a vertically reciprocal movement of the lifter relative to the rider;

e) a shaft rotatably engaged to the rider, wherein the shaft is eccentrically connected to a cam disk so that the shaft rotation generates an eccentric rotation of the cam disk, wherein the cam disk is defined by an inner disk section, an outer ring section, and ball bearings circularly provided between the inner disk section and the outer ring section, wherein an outer rim of the outer ring section abuts to the bottom portion of the lifter, whereby the shaft rotating further generates the vertically reciprocal movement of the lifter relative to the rider in accordance with the eccentric rotation of the cam disk while the outer rim of the outer ring section of the cam disk oscillatingly abuts to the bottom portion of the lifter;

f) massage bumps attached to the top portion of the lifter and moving vertically and/or horizontally along the elongated opening of the elongated top panel of the base frame; and g) a pad covering the massage bumps and the elongated opening of the base frame.

13. The lie-down massager of claim 12 wherein the massage bumps are partitioned to first and second pairs, wherein the first pair bumps are aligned parallel to the second pair bumps.

14. The lie-down massager of claim 12 wherein the massage bumps each include a heater.

15. The lie-down massager of claim 14 wherein the heater is a heating lamp generating heat and infrared rays.

16. The lie-down massager of claim 13 further comprising:

a) first and second bump holders propping and maintaining the first and second pair bumps above the top portion of the lifter, wherein the first and second bump holders are tapered toward each lower end thereof; and b) a first engagement member to rockingly engage the lower ends of the bump holders to the top portion of the lifter.

17. The lie-down massager of claim 16 further comprising a second engagement member to rollingly engage the massage bumps thereto.

18. The lie-down massager of claim 12 wherein the massage bumps are roller balls.

19. The lie-down massager of claim 18 wherein the roller balls are formed of jade.

20. The lie-down massager of claim 12 wherein the cam disk is formed in pair.

21. The lie-down massager of claim 12 wherein the elongated guides are shaped in pins.

22. The lie-down massager of claim 12 further comprising:

a) a motor having a motor shaft parallel to the cam shaft; and b) a timing belt carried on the motor shaft and the cam shaft.

23. A lie-down massager, comprising:

a) a base frame having an elongated top panel, wherein an elongated opening is formed centrally and lengthwisely through the elongated top panel;

b) a pair of rack gears provided below the elongated top panel of the base frame, wherein the rack gears are parallel to each other;

c) a rider having a roller gear perpendicular to the rack gears, wherein the roller gear is rotatably mounted on the rack gears to allow the rider to make a horizontally reciprocal movement along the rack gears, wherein the rider is maintained below the elongated top panel;

d) a pair of roller coasters parallel to each other and to the rack gears, wherein the roller coasters are attached to the base frame and above the roller gear to allow the horizontally moving rider to pass therebetween, wherein the roller coasters each have a substantially waved top surface;

e) a coasting member having a bottom surface and side surfaces, wherein the coasting member is liftedly engaged to the rider, wherein a guide roller is formed outwardly extending from the side surfaces of the coasting member, wherein the guide roller on each of the side surfaces enables the coasting member to make a roller coasting movement on and along the waved top surfaces of the roller coasters while being engagedly lifted from the rider which makes the horizontally reciprocal movement;

f) a lifter having a top portion and a bottom portion, wherein first elongated guides extend marginally from the bottom portion of the lifter, wherein the first elongated guides are releasably received by first guide bushes marginally formed on top of the coasting member to stabilize a vertically reciprocal movement of the lifter relative to the coasting member;

g) a shaft rotatably engaged to the coasting member, wherein the shaft is eccentrically connected to a cam disk so that the shaft rotation generates an eccentric rotation of the cam disk, wherein the cam disk is defined by an inner disk section, an outer ring section, and ball bearings circularly provided between the inner disk section and the outer ring section, wherein an outer rim of the outer ring section abuts to the bottom portion of the lifter, whereby the shaft rotating further generates the vertically reciprocal movement of the lifter relative to the coasting member in accordance with the eccentric rotation of the cam disk while the outer rim of the outer ring section of the cam disk oscillatingly abuts to the bottom portion of the lifter;

h) massage bumps attached to the top portion of the lifter and moving vertically and/or horizontally along the elongated opening of the elongated top panel of the base frame; and i) a pad covering the massage bumps and the elongated opening of the base frame.

24. The lie-down massager of claim 23 wherein the massage bumps are partitioned to first and second pairs, wherein the first pair bumps are aligned parallel to the second pair bumps.

25. The lie-down massager of claim 23 wherein the massage bumps each include a heater.

26. The lie-down massager of claim 25 wherein the heater is a heating lamp generating heat and infrared rays.

27. The lie-down massager of claim 24 further comprising:

a) first and second bump holders propping and maintaining the first and second pair bumps above the top portion of the lifter, wherein the first and second bump holders are tapered toward each lower end thereof; and b) a first engagement member to rockingly engage the lower ends of the bump holders to the top portion of the lifter.

28. The lie-down massager of claim 27 further comprising a second engagement member to rollingly engage the massage bumps thereto.

29. The lie-down massager of claim 23 wherein the massage bumps are roller balls.

30. The lie-down massager of claim 29 wherein the roller balls are formed of jade.

31. The lie-down massager of claim 23 wherein the cam disk is formed in pair.

32. The lie-down massager of claim 23 wherein the first elongated guides are shaped in pins.

33. The lie-down massager of claim 23 further comprises:
   a) second elongated guides extending from the bottom surface of the coasting member; and
   b) second guide bushes upwardly formed on the rider to releasably receive the second elongated guides so as to stabilize the roller coasting movement of the coasting member along the roller coasters and the lifting of the coasting member from the rider.

34. The lie-down massager of claim 23 further comprising:
   a) a motor having a motor shaft parallel to the cam shaft; and
   b) a timing belt carried on the motor shaft and the cam shaft.

35. The lie-down massager of claim 23 wherein the waved top surfaces of the roller coasters each substantially form a curvature of a human spinal cord.

* * * * *